United States Patent [19]

Manogue et al.

[11] Patent Number: 5,516,947
[45] Date of Patent: May 14, 1996

[54] PROCESS FOR CONVERTING CHLORODIFLUOROMETHANE AND/OR DICHLORODIFLUOROMETHANE

[75] Inventors: William H. Manogue, Newark; Charles J. Noelke; Steven H. Swearingen, both of Wilmington, all of Del.

[73] Assignee: E. I. Du Pont de Nemours and Company, Wilmington, Del.

[21] Appl. No.: 427,637

[22] Filed: Apr. 21, 1995

Related U.S. Application Data

[63] Continuation of Ser. No. 212,073, Mar. 11, 1994, abandoned.

[51] Int. Cl.$^6$ .................................................. C07C 17/26
[52] U.S. Cl. ........................................ 570/171; 570/176
[58] Field of Search ................................ 570/176, 171

[56] References Cited

U.S. PATENT DOCUMENTS

| | | | |
|---|---|---|---|
| 2,615,926 | 10/1952 | Benning et al. | 260/653 |
| 2,704,775 | 3/1955 | Clark | 260/653 |
| 3,042,727 | 7/1962 | Olstowski et al. | 260/653 |
| 3,439,052 | 4/1969 | Bjornson | 260/653 |
| 4,861,744 | 8/1989 | Sobolev | 502/227 |
| 5,114,544 | 5/1992 | Forsyth et al. | 204/59 |
| 5,118,492 | 6/1992 | Okazaki et al. | 423/659 |
| 5,185,094 | 2/1993 | Shiflett | 252/67 |
| 5,208,397 | 5/1993 | Manogue et al. | 570/176 |
| 5,300,713 | 4/1994 | Manogue et al. | 570/176 |

FOREIGN PATENT DOCUMENTS

| | | |
|---|---|---|
| 1196345 | 11/1985 | Canada . |
| 0508660 | 3/1992 | European Pat. Off. . |
| 1578933 | 11/1980 | United Kingdom . |
| WO91/05752 | 5/1991 | WIPO . |
| WO91/09000 | 6/1991 | WIPO . |
| WO93/09199 | 5/1993 | WIPO . |

*Primary Examiner*—Alan Siegel

[57] ABSTRACT

A process is disclosed for the conversion of halogenated methanes of the formula $CCl_yH_{2-y}F_2$ (wherein y is 1 or 2) to a mixture of conversion products. The process involves reacting certain halogenated hydrocarbon feeds and hydrogen (wherein said halogenated methanes are at least one mole percent of the halogenated hydrocarbon feed) in a reaction vessel of alumina, silicon carbide or at least one metal selected from gold, chromium, aluminum, molybdenum, titanium, nickel, iron, cobalt, and their alloys at a temperature of from about 500° C. to 800° C. and a pressure from abut 101 kPa to 7000 kPa to produce a mixture of conversion products of said halogenated methanes which comprises at least 5 mole percent $C_2H_2F_4$, wherein the mole ratio of $CH_2FCF_3$ to $CHF_2CHF_2$ in said $C_2H_2F_4$ is at least about 1:9.

20 Claims, 1 Drawing Sheet

PROCESS FOR CONVERTING CHLORODIFLUOROMETHANE AND/OR DICHLORODIFLUOROMETHANE

This is a continuation of application Ser. No. 08/212,073 filed Mar. 11, 1994, now abandoned.

FIELD OF THE INVENTION

This invention relates to processes for the preparation of halogen substituted hydrocarbons and more particularly to processes involving the conversion of halogenated methanes to mixtures of one-carbon and two-carbon hydrofluorocarbons.

BACKGROUND OF THE INVENTION

Halogenated hydrocarbons containing chlorine as well as fluorine have been widely used as refrigerants, propellants, cleaning agents, etc., because of their many remarkable properties such as extremely high chemical stability and physiological inactivity. Useful compositions including such compounds have included R501 (a mixture of $CCl_2F_2$ and $CHClF_2$) and R502 (a mixture of $CHClF_2$ and $CClF_2CF_3$). In recent years there have been concerns over the impact of these chlorine-containing materials on the atmosphere and the environment, and wide-ranging restrictions have been put on their production and use. Accordingly, there has been recent interest in processes which dispose of various halogenated hydrocarbons containing chlorine. One method for their destruction is incineration. However, this method is energy intensive and often produces additional wastes which need to be treated before disposal into the environment. Another method for their disposal involves their catalytic decomposition to mixtures comprising hydrogen chloride, hydrogen fluoride and carbon dioxide (see, e.g., U.S. Pat. No. 5,118,492).

The hydrofluorocarbons difluoromethane (i.e., $CH_2F_2$ or HFC-32) and 1,1,1,2-tetrafluoroethane (i.e., $CH_2FCF_3$ or HFC-134a) have been proposed as a replacement for some chlorofluorocarbons (CFCs), particularly, in refrigeration, air-conditioning and other applications (see, e.g., European Patent Publication No. 508,660 A1 and U.S. Pat. Nos. 4,861,744 and 5,114,544). Compositions containing HFC-32, HFC-134a and 1,1,2,2-tetrafluoroethane (i.e., $CHF_2CHF_2$ or HFC-134) have been found useful as refrigerants, heat transfer media, foam expansion agents, aerosol propellants, solvents and power cycle working fluids (see, e.g., PCT Patent Publication No. WO 93/09199). Compositions containing HFC-32, HFC-134a and/or HFC-134 and pentafluoroethane (i.e., $CHF_2CF_3$, HFC-125) have also been found useful for the same applications as those listed above (see, e.g., U.S. Pat. No. 5,185,094). Accordingly, there is interest in developing efficient processes for the production of the hydrofluorocarbons, HFC-32, HFC-134a, HFC-134, HFC-125 and mixtures thereof. It is evident that methods for converting halogenated hydrocarbons containing chlorine into useful hydrofluoroalkanes would not only remove compounds considered harmful to the environment but in turn would also afford materials, which can be used for refrigerants, propellants, etc., and also have a benign effect on the environment.

Hydrogenolysis is a known method for reducing the chlorine and/or bromine content of halogenated hydrocarbons. For example, U.K. Patent Publication No. 1,578,933 discloses a process for the hydrogenolysis of certain starting materials to tetrafluoroethane using a hydrogenation catalyst (e.g., palladium supported on alumina or carbon). These starting materials are haloethanes containing four or five fluorine atoms. When the organic starting material is $CF_3CCl_2F$ (CFC-114a), $CF_3CH_2F$ (HFC-134a) is obtained almost to the exclusion of $CHF_2CHF_2$ (HFC-134); and when the organic starting material is $CClF_2CClF_2$ (CFC-114) the reaction product usually comprises a mixture of the two tetrafluoroethane isomers. Hydrogenolysis of certain fluorochlorocarbons using tube reactors made of various materials has been disclosed. For example, U.S. Pat. No. 2,615,926 discloses use of platinum tubes, U.S. Pat. No. 2,704,775 discloses use of nickel and stainless steel tubes and U.S. Pat. No. 3,042,727 discloses use of a Vycor® tube. U.S. Pat. No. 5,208,397 discloses the hydrogenolysis of halocarbon mixtures in reactors of silicon carbide and/or a metal selected from aluminum, molybdenum, titanium, nickel, iron or cobalt (or their alloys).

SUMMARY OF THE INVENTION

This invention provides a process for converting halogenated methanes of the formula $CCl_yH_{2-y}F_2$, wherein y is 1 or 2, (i.e., $CHClF_2$ or HCFC-22, and/or $CCl_2F_2$ or CFC-12) to a mixture of conversion products. The process comprises feeding (i) at least one halogenated hydrocarbon of the formula $C_nH_mF_pX_q$ wherein each X is independently selected from the group consisting of chlorine and bromine, n is an integer from 1 to 3, m is an integer from 0 to 7, p is an integer from 0 to 7 and q is an integer from 1 to 7, and wherein said halogenated methanes are at least one mole percent of said halogenated hydrocarbons, and (ii) at least 2 moles of hydrogen per total moles of carbon-chlorine and carbon-bromine bonds in said halogenated hydrocarbons, to a reaction vessel of alumina, silicon carbide or at least one metal selected from the group consisting of gold, chromium, aluminum, molybdenum titanium, nickel, iron, cobalt and their alloys; and reacting said feed in said reaction vessel at a temperature of from about 500° C. to 800° C. and a pressure of from about 101 kPa to 7000 kPa to produce a mixture of conversion products of said halogenated methanes which comprises at least 5 mole percent $C_2H_2F_4$, wherein the mole ratio of $CH_2FCF_3$ to $CHF_2CHF_2$ in said $C_2H_2F_4$ is at least about 1:9.

DETAILED DESCRIPTION OF THE INVENTION

Figure 1:
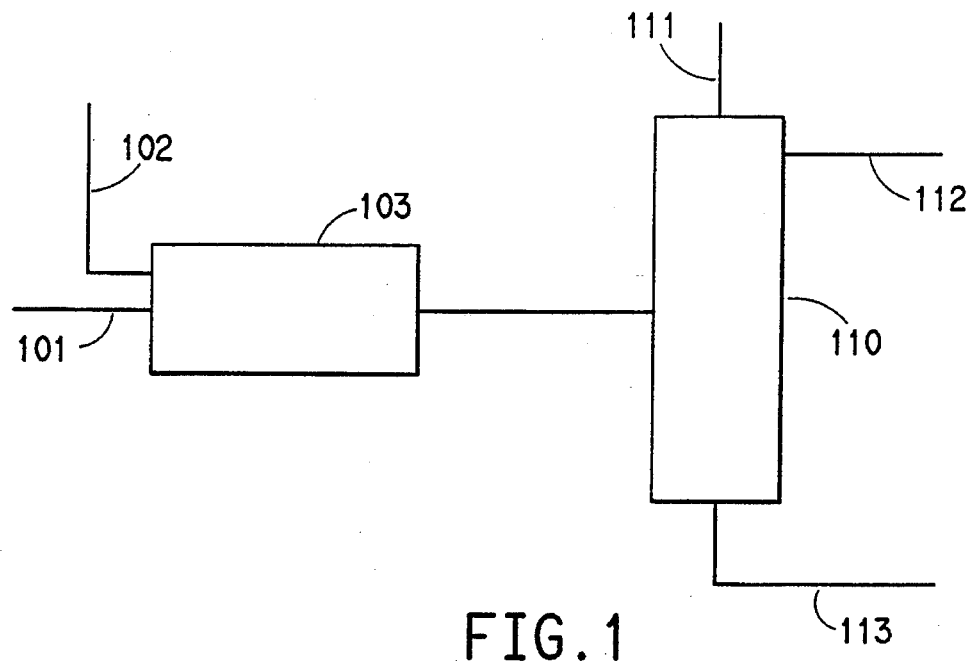
FIG. 1 is a schematic representation of a multiunit process employing a reactor constructed and operated in accordance with this invention.

This invention provides a method of producing useful conversion products of halogenated methanes containing fluorine and chlorine in which the ratio of fluorine atoms to carbon atoms is two (i.e., $CHClF_2$ and/or $CCl_2F_2$). Conversion products as used herein do not include $CHClF_2$ which may be produced as an intermediate when converting initial $CCl_2F_2$ feed. The conversion products include at least 5 mole percent of halogenated ethane products containing fluorine in which the ratio of fluorine atoms to carbon atoms is also two (i.e., $C_2H_2F_4$). If desired, the process can be run to provide a mixture of conversion products which includes at least 10 mole percent $C_2H_2F_4$ wherein the mole ratio of $CH_2FCF_3$ to $CHF_2CHF_2$ in the $C_2H_2F_4$ is at least about 1:9. Normally, $CH_2F_2$ is also produced. If desired, the process can also be run to convert $CHClF_2$ and/or $CCl_2F_2$ to a mixture of conversion products which contains at least 60 mole percent $CH_2F_2$. Essentially pure $CH_2F_2$ can be recovered from unreacted $CHClF_2$, $C_2H_2F_4$ and other products. At lower pressures (e.g., 0 psig (101 kPa) to 50 psig (446 kPa)) and at temperatures of less than 550° C. significant amounts of tetrafluoroethylene can also be produced.

The conversion of this invention is carried out at a temperature range of between about 500° C. and 800° C. and at a pressure of about 0 psig (101 kPa) to about 1000 psig (7000 kPa). The preferred pressure range is from about 0 psig (101 kPa) to about 500 psig (3550 kPa). Production of normally undesirable by-product $CF_3CH_3$ is enhanced at pressures below about 300 psig; and accordingly, pressures from about 300 psig to 500 pisg are particular preferred. Preferably, for the production of $C_2H_2F_4$ the temperature is about 550° C. to 725° C., more preferably, 550° C. to 650° C.

It is desirable to conduct the conversion of this invention in a reaction vessel which is essentially empty. By "essentially empty" is meant empty or empty except for apparatus such as flow distribution apparatus and/or process control apparatus which does not significantly participate in the conversion reaction. Accordingly, essentially empty reaction vessels used in this invention are unpacked and are particularly distinguished from reactors which are packed with conventional hydrogenation catalysts.

As indicated above, the conversion of this invention is conducted in a reaction vessel of selected materials. Such reaction vessels may also include other materials of construction as long as the surfaces which contact the feed during the reaction are of the indicated material. Accordingly, the conversion of the $CHClF_2$ and/or $CCl_2F_2$ is conducted in the presence of alumina or silicon carbide or at least one metal selected from gold, chromium, aluminum, molybdenum, titanium, nickel, iron, cobalt and their alloys. The metals may be coated on the inside surface of a reaction vessel (e.g., by plating or sputtering the metals or their alloys onto the inside surface). Such coating can help to minimize corrosion of the reaction vessel well. A chrome-plated reactor is an example of such a reaction vessel. As noted above, an essentially empty reaction vessel is normally employed (i.e., an unpacked vessel which may still contain internals commonly used in empty reactors such as thermocouples and flow distributors such as baffles).

When reference is made to alloys of the metals used in this invention, it is meant a nickel alloy containing from 1 to 99.9% by weight nickel, a cobalt alloy containing 1 to 99.9% by weight cobalt, an iron alloy containing 0.2 to 99.9% by weight iron, a molybdenum alloy containing 70 to 99.9% by weight molybdenum, an aluminum alloy containing 80 to 99.9% by weight aluminum, a gold alloy containing 0.2 to 99.9% by weight gold, and a titanium alloy containing 72 to 99.8% by weight titanium. Preferably the remainder of these alloys is selected such that the alloy consists essentially of (i) one or more metals selected from aluminum, molybdenum, titanium, nickel, iron and cobalt, and optionally (ii) chromium and/or tungsten. Particularly preferred for the practice of this invention are nickel or alloys of nickel such as those containing from about 44% to 80% nickel (e.g., Inconel® 600 alloy, Inconel® 617 alloy, Inconel® 625 alloy or Hastelloy® C276 alloy). Suitable nickel alloys include those which contain in addition to nickel, at least one metal selected from Cr, Fe, Co, Mo, W, Nb, Ti, Al, Mn, Cu, V, La, Ti and Zr. They may also contain C, Si and B.

The halogenated hydrocarbons fed to the reaction vessel may consist essentially of halogenated fluoromethanes of the formula $CCl_yH_{2-y}F_2$. Indeed, mixtures of these compounds represent suitable starting materials (e.g., refrigerant R-501). Such feed may also contain substantially inert materials such as nitrogen, and non-reactive hydrocarbons (e.g., $CH_4$ and $C_2H_6$) and hydrofluorocarbons (e.g., $CH_2F_2$ and $CH_3CHF_2$).

Alternatively, mixtures with other saturated and/or olefinic halogenated hydrocarbons containing chlorine and/or bromine of the formula $C_nH_mF_pX_q$ may also be used. Treatment of mixtures containing one or more replaced chlorine and/or bromine-containing refrigerant compounds such as those listed in ASHRAE Handbook (1985 Fundamentals) at pages 16.3 and 16.4 are of note. These include, for example, $CCl_3F$, $CClF_3$, $CBrF_3$, $CHCl_2F$, $CH_2ClF$, $CCl_2FCClF_2$, $CCl_3CClF_2$, $CCl_2FCClF_2$, $CCl_3CF_3$, $CCl_2FCF_3$, $CClF_2CClF_2$, $CBrF_2CBrF_2$, $CClF_2CF_3$, $CHCl_2CF_3$, $CHClFCF_3$, $CHF_2CClF_2$, $CH_2ClCF_3$, $CH_3CCl_3$, $CH_3CClF_2$, $CCl_2=CF_2$, and $CClF=CF_2$. Of particular note are mixtures which contain $CClF_2CF_3$ and $CHClF_2$ (e.g., R-502) and mixtures which contain $CCl_2F_2$ and $CH_2ClF$ (e.g., R-505). These other bromine and/or chlorine-containing halogenated hydrocarbons may undergo hydrogenolysis as the conversion of halogenated methanes according to this invention proceeds. In this regard, reference is made to PCT Patent Publication No. WO 91/05752. The conversion of this invention is especially evident where the total amount of halogenated methanes of the formula $CCl_yH_{2-y}F_2$ is at least about 10 mole percent of said halogenated hydrocarbons of the formula $C_nH_mF_pX_q$ fed to the reaction vessel; with particular benefit of the conversion being realized where said halogenated methanes are at least about 25 mole percent of said halogenated hydrocarbons, especially where said halogenated methanes are at least about 50 mole percent of said halogenated hydrocarbons. Treatment of mixtures of halogenated hydrocarbons in accordance with this invention can thus be utilized in connection with a disposal process for unwanted halogenated hydrocarbons containing chlorine and/or bromine. Of particular note is treatment of mixtures of halogenated hydrocarbons containing chlorine (i.e., embodiments where X is Cl).

Of particular note are feed mixtures comprising (in addition to $CCl_2F_2$ and/or $CHClF_2$) $CClF_2CF_3$ which result in product mixtures including $CH_2F_2$, $CH_2FCF_3$ and $CHF_2CF_3$ (and normally $CHF_2CHF_2$); and feed mixtures comprising (in addition to $CCl_2F_2$ and/or $CHClF_2$) $CCl_2FCF_3$ and/or $CHClFCF_3$ which provide product mixtures including $CH_2F_2$ and $CH_2FCF_3$ in which the mole ratio of $CH_2FCF_3$ to $CH_2F_2$ is enhanced from that obtained merely by the conversion of $CCl_yH_{2-y}F_2$. Indeed, it will be evident that products having varying ratios of $CH_2F_2$, $CH_2FCF_3$, and $CHF_2CF_3$ can be produced by varying the relative amounts of $CCl_yH_{2-y}F_2$, $CClF_2CF_3$ and $CHClFCF_3$ and/or $CCl_2FCF_3$ feed to the reaction vessel.

Also of note are embodiments of this invention where tetrafluoroethylene, $CH_2F_2$ and $C_2H_2F_4$ are all produced from $CHClF_2$ and/or $CCl_2F_2$. In these embodiments, the $C_2H_2F_4$ can be separated from the $CH_2F_2$ and $CF_2=CF_2$. If desired, the $CF_2=CF_2$ can be reacted with HF to provide $CHF_2CF_3$. The hydrofluorination of tetrafluoroethylene may be conducted with or without prior separation of other products (e.g., $C_2H_2F_4$).

Also of note are embodiments of this invention where HFC-236ca (i.e., $CF_2HCF_2CF_2H$), $CH_2F_2$ and $C_2H_2F_4$ are all produced from $CHClF_2$ and/or $CCl_2F_2$. Lower ratios of $H_2$ (e.g., about 2 moles $H_2$ per mole C—Cl bond) normally favor production of $CF_2HCF_2CF_2H$.

The amount of hydrogen contacted with the gaseous $CCl_yH_{2-y}F_2$, and optionally other halofluorocarbons such as $CClF_2CF_3$ undergoing hydrogenolysis, should be at least 2.0 moles per mole of C—X bond (i.e., carbon-chlorine and carbon-bromine bonds). In general, the amount of hydrogen preferably ranges from 2 to 60 moles per mole of C—X bond, and more preferably ranges from 10 to 30 moles per mole of C—X bond. The hydrogen can be fed either in the pure state or diluted with a substantially inert gas (e.g., nitrogen, methane, or difluoromethane). Preferably, for high selectivities, hydrogen is added in sufficient amounts to provide a reactor effluent containing at least about 0.5 mole percent hydrogen. Normally less hydrogen is needed for reacting $CHClF_2$ compared to $CCl_2F_2$ (and consequently there is normally less HCl formation when $CHClF_2$ is used rather than $CCl_2F_2$).

Preferably, in the process of this invention the yield loss from $CCl_2F_2$ and $CHClF_2$ to non-halocarbons, (e.g., $CH_4$, $C_2H_6$ or carbon) is less than 10%. The process can be operated such that the formation of solids in the reaction vessel is low, thus permitting long-term operation with infrequent plugging.

The extent of the replacement of chlorine and/or bromine by hydrogen increases with reaction time. Reaction times between 0.1 seconds and 25 minutes are preferred. Most preferred are reaction times between 0.2 and 4 minutes. The reaction time will generally be inversely related to the reaction temperature.

Preferably the reaction time and temperature are selected to obtain long term (e.g., greater than about 1000 hours) plug free operation and to provide as the major products of the conversion, products which retain the original ratio of fluorine to carbon of 2:1. Although substantial conversions can be achieved in a once-through system, recycle of unreacted $CCl_2F_2$ and/or $CHClF_2$ (or of the intermediate $CHClF_2$ when $CCl_2F_2$ feed is used) can be employed in a conventional manner. Inert materials and inert products such as $CH_2F_2$ and HCl can be recycled as desired. In many embodiments the combined yield losses to other materials are less than 10%.

The products of the reaction can be separated and purified by conventional means (e.g., distillation and sorption). The products can be used as solvents, blowing agents, refrigerants and propellants.

FIG. 1 illustrates employment of the instant invention in a multiunit method for producing $C_2H_2F_4$ along with a purified mix of $CH_2F_2$ (HFC-32) and $CHF_2CF_3$ (HFC-125). Tetrafluoroethanes (i.e., HFC-134 and HFC-134a) are produced in this process with the ratio of HFC-134a to HFC-134 being at least 1:9. HFC-32, HFC-125, HFC-134 and HFC-134a can then be blended to prepare constant boiling compositions which are useful as refrigerants, heat transfer media, gaseous dielectrics, fire extinguishing agents, foam expansion agents, aerosol propellants, and as power cycle working fluids (see U.S. Pat. No. 5,185,094). In the illustrated method, a mixture of $CHClF_2$ and $CClF_2CF_3$ from feedline (101) is fed along with hydrogen from feedline (102) to a reactor (103) constructed and operated in accordance with this invention. The converted products are fed to a separation system such as distillation column (110) with HCl, hydrogen and some $CHF_2CF_3$ and $CClF_2CF_3$ being removed through top line (111), with a mixture consisting essentially of $CHF_2CHF_2$, $CH_2FCF_3$ and some $CHClF_2$ being withdrawn near bottom line (113), and a mixture of $CH_2F_2$, $CHF_2CF_3$ and some $CClF_2CF_3$ being withdrawn near the top line (112).

Figure 2:
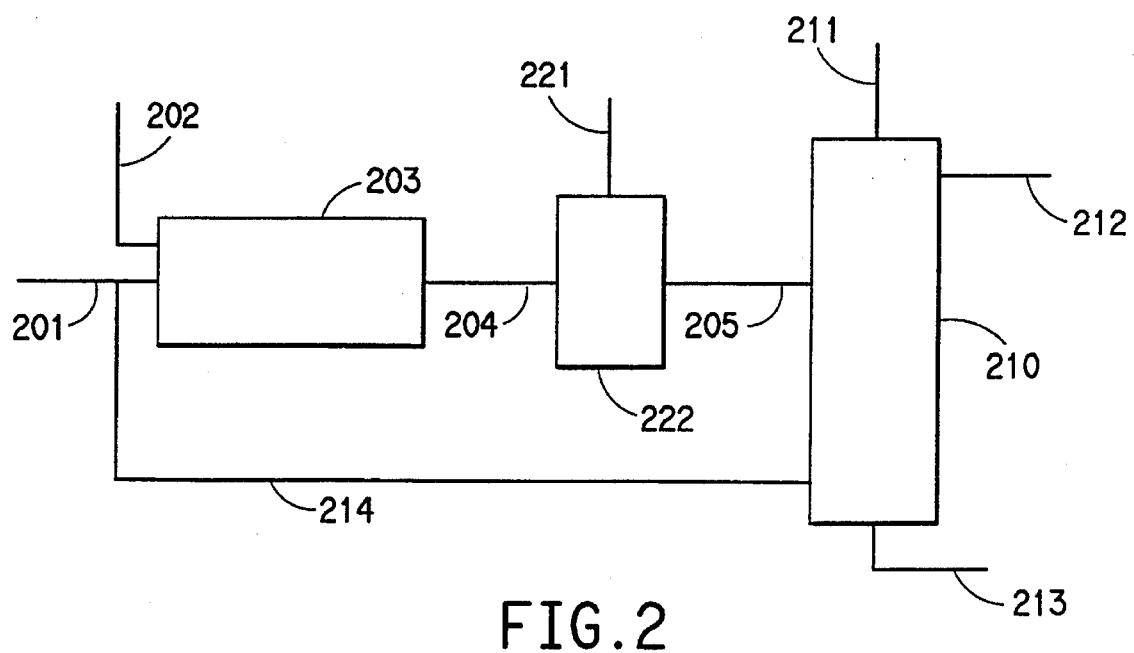
FIG. 2 is a schematic representation of a multiunit process employing a reactor constructed and operated in accordance with this invention.

FIG. 2 illustrates employment of the instant invention in another multiunit method for producing a purified mix of $CH_2F_2$ and $CHF_2CF_3$. Tetrafluoroethanes (i.e., $CHF_2CHF_2$ and $CH_2FCF_3$) are also produced in this process. In the illustrated method, $CCl_2F_2$ from feedline (201) is fed along with hydrogen from feedline (202) to a reactor (203) constructed and operated in accordance with this invention to produce significant amounts of $CF_2=CF_2$ as well as $C_2H_2F_4$ and $CH_2F_2$. The products of reactor (203) are fed to another reactor (222) and contacted therein with HF fed through line (221). In reactor (222) HF is reacted with tetrafluoroethylene in the presence of a chromium catalyst (e.g., according to the procedure disclosed in Canadian Patent, 1,196,345) to yield $CHF_2CF_3$. All the reaction products are fed through line (205) to a separation system such as distillation column (210) with HCl, hydrogen and residual $CF_2=CF_2$ being removed through line (211), with a mixture consisting essentially of HF, $CHF_2CHF_2$ and $CH_2FCF_3$ being withdrawn through line (213), with $CHClF_2$ being withdrawn through line (214) and recycled to reactor (203), and with a mixture of $CH_2F_2$ and $CHF_2CF_3$ being withdrawn through line (212).

Practice of this invention will become further apparent from the following non-limiting examples.

EXAMPLE 1

A flow reactor under microprocessor control was used. The reactor was a 3/8 in. (1 cm) by 15 in. (38 cm) Inconel™ 600 nickel alloy lined with 0.08 in. (0.2 cm) gold U-tube flow reactor operated at a pressure of 300 psig (2170 kPa), immersed in a fluidized sandbath and heated to temperatures of up to 600° C.

Hydrogen gas was metered into the system through mass flow controllers. Liquid halocarbons were fed through a syringe pump and vaporized before entering the reactor. Conversion and yields were measured by taking gas stream samples into a gas chromatograph. Product identification was by GC retention times with off-line sampling by GC/Mass-Spec and GC/IR to confirm peak identification.

The example demonstrates a single-pass hydrogenolysis and reports only major hydrogenolysis products and unreacted $CHClF_2$. One skilled in the art will recognize that $CHClF_2$ can be separated from the reaction products and recycled in accordance with this invention.

The results are shown in the following Table 1 where F22 is $CHClF_2$, F32 is $CH_2F_2$, F134 is $CHF_2CHF_2$, F134a is $CH_2FCF_3$, and $\Sigma$Sel. to Prod. is the sum of the mole percent of F32, F134 and F134a, and R.T. is the reaction time.

TABLE 1

| T | Mol. Ratio | R.T. | % Carbon | % F22 | % Selectivity to | | | |
|---|---|---|---|---|---|---|---|---|
| °C. | H2:F22 | min. | Balance | Conv. | F32 | F134 | F134a | CH$_4$ |
| 500 | 28.6 | 0.36 | 92 | 12.1 | 76 | 15.3 | 2.7 | 2.7 |
| 500 | 24.5 | 0.34 | 105 | 10.5 | 74 | 14.3 | 2.7 | 3.0 |
| 500 | 13.2 | 0.65 | 89 | 13.8 | 76 | 12.3 | 2.4 | 3.4 |
| 500 | 11.5 | 0.32 | 114 | 8.1 | 71 | 15.1 | 2.9 | 2.7 |
| 500 | 11.4 | 0.35 | 90 | 8.5 | 70 | 16.1 | 3.1 | 3.0 |
| 500 | 8.8 | 0.32 | 112 | 7.3 | 68 | 15.6 | 3.0 | 2.6 |

TABLE 1-continued

| T °C. | Mol. Ratio H2:F22 | R.T. min. | % Carbon Balance | % F22 Conv. | % Selectivity to | | | |
|---|---|---|---|---|---|---|---|---|
| | | | | | F32 | F134 | F134a | CH$_4$ |
| 500 | 5.9 | 0.60 | 112 | 9.4 | 68 | 14.0 | 2.7 | 3.3 |
| 540 | 28.6 | 0.34 | 110 | 33.7 | 77 | 16.9 | 2.9 | 1.3 |
| 540 | 25.4 | 0.17 | 99 | 23.5 | 72 | 19.1 | 3.7 | 1.4 |
| 540 | 24.6 | 0.32 | 101 | 31.6 | 77 | 16.2 | 3.0 | 1.2 |
| 540 | 14.3 | 0.33 | 99 | 26.7 | 74 | 17.2 | 3.3 | 1.2 |
| 540 | 13.6 | 0.16 | 115 | 18.3 | 68 | 20.9 | 4.0 | 0.9 |
| 570 | 41.2 | 0.31 | 92 | 64.9 | 77 | 17.4 | 2.9 | 1.3 |
| 570 | 19.0 | 0.33 | 92 | 56.5 | 74 | 19.5 | 3.2 | 0.9 |
| 570 | 17.1 | 0.33 | 118 | 51.6 | 72 | 20.2 | 3.3 | 0.8 |
| 570 | 15.3 | 0.60 | 113 | 59.8 | 74 | 18.3 | 2.9 | 1.5 |
| 570 | 14.6 | 0.15 | 92 | 39.6 | 68 | 22.9 | 4.1 | 0.8 |
| 570 | 6.1 | 0.56 | 117 | 48.5 | 70 | 18.9 | 3.1 | 1.0 |
| 600 | 38.0 | 0.32 | 90 | 86.7 | 75 | 19.1 | 3.5 | 1.4 |
| 600 | 23.0 | 0.30 | 92 | 81.4 | 73 | 20.3 | 3.6 | 1.0 |
| 600 | 20.8 | 0.16 | 109 | 69.1 | 67 | 24.5 | 4.5 | 1.3 |
| 600 | 15.3 | 0.15 | 118 | 64.3 | 66 | 24.9 | 4.5 | 0.6 |
| 600 | 15.3 | 0.16 | 119 | 63.9 | 63 | 26.0 | 4.7 | 1.4 |
| 600 | 13.0 | 0.14 | 110 | 60.6 | 64 | 26.1 | 4.7 | 0.6 |
| 600 | 13.0 | 0.29 | 91 | 74.4 | 67 | 23.3 | 4.2 | 2.1 |
| 600 | 9.8 | 0.28 | 110 | 67.6 | 60 | 25.7 | 4.6 | 2.6 |
| 600 | 3.0 | 0.94 | 103 | 68.8 | 62 | 23.1 | 3.4 | 0.7 |
| 630 | 48.7 | 0.16 | 97 | 93.1 | 68 | 22.8 | 4.8 | 2.4 |
| 630 | 23.9 | 0.31 | 103 | 93.5 | 70 | 22.4 | 4.5 | 1.2 |
| 630 | 5.8 | 0.52 | 80 | 92.3 | 67 | 23.3 | 4.1 | 1.1 |

EXAMPLE 2

A flow reactor under microprocessor control was used. The reactor was a ⅜ in. (1 cm) by 15 in. (38 cm) Inconel™ 617 nickel alloy U-tube flow reactor operated at a pressure of 300 psig (2170 kPa), immersed in a fluidized sandbath and heated to temperatures of up to 600° C.

The reaction procedure and the analysis of reaction products were the same as those used in Example 1. In this example, the molar ratio of H$_2$:CHClF$_2$ was 17:1 in the three runs.

The results are shown in Table 2, where the abbreviations have the same meaning as those in Table 1.

TABLE 2

| Temp °C. | R.T. min. | % Carbon Balance | % F22 Conv. | % Selectivity to | | | |
|---|---|---|---|---|---|---|---|
| | | | | F32 | F134 | F134a | CH$_4$ |
| 540 | 0.34 | 66 | 56 | 72 | 16 | 2.3 | 6.0 |
| 570 | 0.32 | 80 | 75 | 72 | 18 | 3.1 | 4.0 |
| 600 | 0.31 | 96 | 90 | 67 | 21 | 3.7 | 4.0 |

EXAMPLE 3

A mixture of CHClF$_2$ (HCFC-22) and hydrogen at a molar ratio of H$_2$:HCFC-22 of 16:1 was fed to a ⅜ in. (1 cm) by 15 in. (38 cm) Inconel™ 617 nickel alloy U-tube flow reactor operated at a pressure of 300 psig (2170 kPa), immersed in a fluidized sandbath and heated to temperatures of between 460° C. and 630° C. Various feed rates were used and the reactor effluent was sampled hourly using an on-line gas chromatograph.

For a 10 hour period between 140 and 150 hours in synthesis, at a temperature of 600° C. and a reaction time of 0.64 minutes, the average conversion of HCFC-22 was 94.4%. The selectivity to CH$_2$F$_2$ (HFC-32) was 69.4%; to CHF$_2$CHF$_2$ (HFC-134) was 19.1%; to CH$_2$FCF$_3$ (HFC-134a) was 3.1%; and to methane was 5.2%. The carbon balance for this period was 91.3%.

EXAMPLE 4

Alumina Tube

The reactor was a ½ in. (1.3 cm) OD by 12 in. (30 cm) length alumina tube and was heated in a tube furnace equipped with a nickel liner to provide even heating.

The reaction procedure and the analysis of reaction products were the same as those used in Example 1. In this example, the molar ratio of H$_2$:CHClF$_2$ was 6:1 in the two runs and the reaction pressure was atmospheric (101 kPa).

The results are shown in Table 3, where the abbreviations have the same meaning as those in Table 1 and TFE is CF$_2$=CF$_2$ except that ΣSel. to Prod. is the sum of the mole percent of F32, F134, F134a and TFE.

TABLE 3

| Temp °C. | R.T. min. | % Carbon Balance | % F22 Conv. | % Selectivity to | | | | |
|---|---|---|---|---|---|---|---|---|
| | | | | F32 | TFE | F134 | F134a | CH$_4$ |
| 570 | 0.27 | 111 | 65 | 14.0 | 34.6 | 13.6 | 19.7 | 0.1 |

TABLE 3-continued

| Temp °C. | R.T. min. | % Carbon Balance | % F22 Conv. | % Selectivity to | | | | |
|---|---|---|---|---|---|---|---|---|
| | | | | F32 | TFE | F134 | F134a | CH$_4$ |
| 600 | 0.52 | 77 | 93 | 27.0 | 1.8 | 23.3 | 34.0 | 0.3 |

EXAMPLE 5

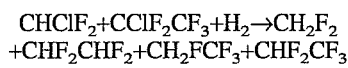

A mixture of R502 (R502 is a commercial refrigerant containing 51.2 weight percent CClF$_2$CF$_3$ (CFC-115) and 48.8% CHClF$_2$ (HCFC-22)) and H$_2$ at molar ratio of H$_2$:R502 of 15 was fed to a ⅜ in. (1 cm) OD by 15 in. (38 cm) Inconel™ U-tube with a 0.080 in. (0.2 cm) gold liner. The reactor was operated at 300 psig (2170 kPa) and was immersed in a fluidized bed heater. For a period of seven hours at about 100 hours in synthesis, with a liquid feed rate of 1.0 mL/hr of R502 and a hydrogen feed rate of 62 standard cubic centimeters per minute (1.0×10$^{-6}$ m$^3$/s), at a reactor temperature of 630° C., the average conversion of CFC-115 to HFC-125 was 94.5% and the average conversion of HCFC-22 to mixed products was 92.0%. The selectivity to HFC-32 was 70.7%, selectivity to HFC-134 was 19.7%, to HFC-134a was 3.7%, to CH$_3$CF$_3$ (HFC-143a) was 0.1%, and to methane was 2.6%.

EXAMPLE 6

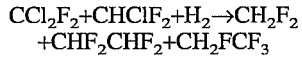

A mixture of a 1:1 molar ratio of CCl$_2$F$_2$ (CFC-12) and CHClF$_2$ (HCFC-22) and H$_2$ at molar ratio of H$_2$:[CFC-12+HCFC-22] of 34.7:1 was fed to a ⅜ in. (1 cm) OD by 15 in. (38 cm) Inconel™ U-tube with a 0.080 in. (0.2 cm) gold liner. The reactor was operated at 300 psig (2170 kPa) and was immersed in a fluidized bed heater. The reaction time for the 500°, 540°, and 570° C. runs was 10 seconds, for the 600° and 630° C. runs, 9 seconds. The analysis was the same as that described in Example 1 and is shown in Table 4.

TABLE 4

| Temp. °C. | % Conv. of | | % Selectivity to | | | | |
|---|---|---|---|---|---|---|---|
| | F12 + F22 | F12 | F32 | F134 | F134a | TFE | CH$_4$ |
| 500 | 8.6 | 1.2 | 58.1 | 4.2 | 0.8 | 1.1 | 23.0 |
| 540 | 18.0 | 38.4 | 76.9 | 13.2 | 2.5 | 0.4 | 3.9 |
| 570 | 49.2 | 88.0 | 81.6 | 12.7 | 2.5 | 0.1 | 1.4 |
| 600 | 72.2 | 98.5 | 78.9 | 15.1 | 2.9 | 0.0 | 0.7 |
| 630 | 91.8 | 100 | 76.7 | 17.1 | 3.5 | 0.0 | 0.7 |

EXAMPLE 7

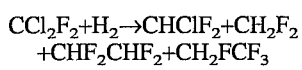

A mixture of CCl$_2$F$_2$ (CFC-12) and H$_2$ at molar ratio of H$_2$:CFC-12 of 16:1 was fed to a ⅜ in. (1 cm) OD by 15 in. (38 cm) Inconel™ U-tube with a 0.080 in. (0.2 cm) gold liner. The reactor was operated at 300 psig (2170 kPa) and was immersed in a fluidized bed heater. The analysis was the same as that described in Example 1 and is shown in Table 5.

TABLE 5

| Temp °C. | R.T. min. | % F12 Conv. | % Selectivity to | | | | |
|---|---|---|---|---|---|---|---|
| | | | F22 | F32 | F134 | F134a | CH$_4$ |
| 450 | 0.44 | 1.7 | 35.3 | 16.9 | 0.0 | 0.0 | 32.7 |
| 500 | 0.41 | 2.6 | 0.2 | 12.9 | 0.0 | 0.0 | 30.2 |
| 500 | 0.83 | 11.5 | 79.6 | 5.0 | 0.0 | 0.0 | 7.2 |
| 540 | 0.39 | 29.9 | 91.4 | 4.1 | 0.0 | 0.0 | 2.6 |
| 540 | 0.79 | 59.4 | 87.5 | 8.5 | 0.5 | 0.1 | 1.8 |
| 570 | 0.38 | 75.9 | 82.3 | 13.3 | 1.5 | 0.3 | 0.9 |
| 570 | 0.76 | 100 | 64.0 | 29.0 | 1.9 | 0.4 | 1.0 |
| 600 | 0.37 | 99.2 | 48.4 | 42.9 | 4.9 | 1.0 | 0.7 |
| 600 | 0.73 | 100 | 29.2 | 60.3 | 5.9 | 1.1 | 1.3 |

EXAMPLE 8

A flow reactor consisting of a ¾ in. (1.9 cm) schedule 40 pipe made of Hastelloy™ 276 nickel alloy and approximately 100 ft. (30.5 m) in length that was coil shaped was used. The coil reactor was immersed in a high temperature sand bath for temperature control. Fresh and recycled hydrogen (the recycled hydrogen contained between 1.2% to 4% methane) was heated in a jacketed coil with steam at 165 psig (1240 kPa). The recycle and make-up system providing hydrogen to the reactor consisted of a KOH scrubber, dryer, compressor and low-temperature liquefaction system operating at 400 psig (2860 kPa) and −40° C. The CHClF$_2$ (HCFC-22) was pumped as a liquid through a mass flow controller and then through a 165 psig (1240 kPa) steam jacketed coil to vaporize the HCFC-22. The hydrogen and HCFC-22 streams were then joined and passed through a static mixer before entering the high temperature reactor which was maintained at 610° C. The hydrogen flow was 45 L/min. and the HCFC-22 flow was 4.5 lb/hr (2.04 kg/hr). The H$_2$:CHClF$_2$ mole ratio was about 5.1:1.

The steady state organic composition of the reactor effluent, run under the above-described conditions, was found to consist of the following reported in area %; CH$_4$, 8% (the hydrogen fed to the reactor contained 1 to 4% CH$_4$); CH$_2$F$_2$, 38%; CH$_2$FCF$_3$, 1.3%; CHF$_2$CHF$_2$, 27%; CHClF$_2$, 7%; CHF$_2$CClF$_2$, 5.5%; CHF$_2$CF$_2$CHF$_2$, 5.5%. Other products found include H(CF$_2$)$_4$H, CHF$_3$, CH$_3$F, C$_3$HClF$_6$, C$_4$Cl$_2$F$_8$, CH$_2$ClF, CClF$_2$CClF$_2$, CCl$_2$FCF$_3$ and CCl$_2$F$_2$.

EXAMPLE 9

A flow reactor consisting of a 1 in. (2.54 cm) schedule 40 pipe made of Hastelloy™ 276 nickel alloy and approximately 100 ft (30.5 m) in length that was coil shaped was used. The coil reactor was immersed in a high temperature sand bath for temperature control. Fresh and recycled hydrogen (the recycled hydrogen contained between 1.2% to 4% methane) was heated in a jacketed coil with steam at 165 psig (1240 kPa). The CHClF$_2$ (HCFC-22) was pumped as a liquid through a mass flow controller and then through a 165 psig (1240 kPa) steam jacketed coil to vaporize the HCFC-22. The hydrogen and HCFC-22 streams were then joined and passed through a static mixer before entering the high temperature reactor which was maintained at 600° C. The hydrogen flow was 190 L/min. and the HCFC-22 flow was 27.5 lb/hr (12.5 kg/hr). The $H_2$:$CHClF_2$ mole ratio was about 3.5:1.

The hot reactor effluent was cooled before introducing it into a caustic (10 wt. % NaOH was used) scrubber at 20–40 psig (240–380 kPa). The reactor off-gas was sampled on-line, before the scrubber, about once an hour. Product analyses of runs at various pressures, reported in area %, are shown in Table 6.

TABLE 6

| Pressure psig (kPa) | % F22 | % F32 | % F134 | % F134a | % F143a[a] | % F1114[b] |
|---|---|---|---|---|---|---|
| 80 (650) | 27.3 | 14.8 | 25.3 | 9.9 | 1.4 | 0.7 |
| 150 (1140) | 20.1 | 25.0 | 27.3 | 7.3 | 1.0 | 0.2 |
| 200 (1480) | 17.8 | 32.0 | 29.2 | 6.3 | 0.6 | |
| 240 (1760) | 14.2 | 35.4 | 30.2 | 6.0 | 0.7 | |
| 270 (1960) | 14.8 | 35.2 | 27.1 | 4.6 | 0.8 | 0.1 |
| 300 (2170) | 12.8 | 40.2 | 29.5 | 4.9 | 0.6 | |
| 315 (2270) | 12.4 | 40.2 | 29.6 | 4.8 | 0.6 | 0.1 |

[a]F143a = $CH_3CF_3$
[b]F1114 = $CF_2$=$CF_2$

Other products found include $CH_4$, $CHF_2CF_2CHF_2$, $CHF_2CClF_2$, $H(CF_2)_4H$, $CHF_3$, $CH_3F$, $C_3HClF_6$, $C_4Cl_2F_8$, $CH_2ClF$, $CClF_2CClF_2$, $CCl_2FCF_3$ and $CCl_2F_2$.

What is claimed is:

1. A process for the conversion of halogenated methanes of the formula $CCl_yH_{2-y}F_2$, wherein y is 1 or 2 to produce $C_2H_2F_4$ therefrom comprising:

feeding (i) at least one reactant consisting essentially of said halogenated methanes and optionally at least one additional halogenated hydrocarbon of the formula $C_nH_mF_pX_q$ wherein each X is independently selected from chlorine and bromine, n is an integer from 1 to 3, m is an integer from 0 to 7, p is an integer from 0 to 7 and q is an integer from 1 to 7, and wherein said halogenated methanes are at least 1 mole percent of the total of said halogenated hydrocarbons and said halogenated methanes, and (ii) at least 2 moles of hydrogen per total moles of carbon-chlorine and carbon-bromine bonds in said halogenated hydrocarbons and said halogenated methanes, to a reaction vessel of alumina, silicon carbide or at least one metal selected from the group consisting of gold, chromium, aluminum, molybdenum, titanium, nickel, iron, cobalt, and their alloys; and reacting said feed in said reaction vessel at a temperature of from about 500° C. to 800° C. and a pressure of from about 101 kPa to 7000 kPa to produce a mixture of conversion products of said halogenated methanes which comprises at least 5 mole percent $C_2H_2F_4$, wherein the mole ratio of $CH_2FCF_3$ to $CHF_2CHF_2$ in said $C_2H_2F_4$ is at least about 1:9.

2. The process of claim 1 wherein the reaction vessel is an essentially empty reaction vessel; wherein the feed is reacted at a temperature of from about 550° C. to 725° C.; and wherein the mixture of conversion products includes at least 10 mole percent $C_2H_2F_4$ wherein the mole ratio of $CH_2FCF_3$ to $CHF_2CHF_2$ in the $C_2H_2F_4$ is at least about 1:9.

3. The process of claim 2 wherein the halogenated hydrocarbons fed to the reaction vessel consist essentially of said halogenated methanes.

4. The process of claim 2 wherein the halogenated hydrocarbons fed to the reaction vessel comprise $CClF_2CF_3$.

5. The process of claim 2 wherein the halogenated hydrocarbons fed to the reaction vessel comprise at least one of $CCl_2FCF_3$ and $CHClFCF_3$.

6. The process of claim 2 wherein the temperature is less than 550° C. and the pressure is from 101 kPa to 446 kPa; and wherein tetrafluoroethylene is produced.

7. The process of claim 2 wherein the mixture of the conversion products of said halogenated methanes contains at least 60 mole percent $CH_2F_2$.

8. The process of claim 2 wherein the halogenated hydrocarbons fed to the reactor comprise one or more compounds selected from the group consisting of $CCl_3F$, $CClF_3$, $CBrF_3$, $CHCl_2F$, $CH_2ClF$, $CCl_2FCCl_2F$, $CCl_3CClF_2$, $CCl_2FCClF_2$, $CCl_3CF_3$, $CCl_2FCF_3$, $CClF_2CClF_2$, $CBrF_2CBrF_2$, $CClF_2CF_3$, $CHCl_2CF_3$, $CHClFCF_3$, $CHF_2CClF_2$, $CH_2ClCF_3$, $CH_3CCl_3$, $CH_3CClF_2$, $CCl_2$=$CF_2$, and $CClF$=$CF_2$.

9. The process of claim 8 wherein said halogenated methanes are at least about 25 mole percent of the halogenated hydrocarbons fed to the reaction vessel.

10. The process of claim 9 wherein the reaction vessel is of alumina.

11. The process of claim 1 wherein the halogenated hydrocarbons fed to the reaction vessel consist essentially of said halogenated methanes.

12. The process of claim 1 wherein the halogenated hydrocarbons fed to the reaction vessel comprise $CClF_2CF_3$.

13. The process of claim 1 wherein the halogenated hydrocarbons fed to the reaction vessel comprise at least one of $CCl_2FCF_3$ and $CHClFCF_3$.

14. The process of claim 1 wherein the temperature is less than 550° C. and the pressure is from 101 kPa to 446 kPa; and wherein tetrafluoroethylene is produced.

15. The process of claim 1 wherein the mixture of the conversion products of said halogenated methanes contains at least 60 mole percent $CH_2F_2$.

16. The process of claim 1 wherein the halogenated hydrocarbons fed to the reactor comprise one or more compounds selected from the group consisting of $CCl_3F$, $CClF_3$, $CBrF_3$, $CHCl_2F$, $CH_2ClF$, $CCl_2FCCl_2F$, $CCl_3CClF_2$, $CCl_2FCClF_2$, $CCl_3CF_3$, $CCl_2FCF_3$, $CClF_2CClF_2$, $CBrF_2CBrF_2$, $CClF_2CF_3$, $CHCl_2CF_3$, $CHClFCF_3$, $CHF_2CClF_2$, $CH_2ClCF_3$, $CH_3CCl_3$, $CH_3CClF_2$, $CCl_2$=$CF_2$, and $CClF$=$CF_2$.

17. A process for the conversion of $CHClF_2$ to $C_2H_2F_4$, comprising:

feeding (i) said $CHClF_2$, and (ii) at least 2 moles of hydrogen per total moles of carbon-chlorine bonds in said $CHClF_2$, to a reaction vessel of alumina, silicon carbide or at least one metal selected from the group consisting of gold, chromium, aluminum, molybdenum, titanium, nickel, iron, cobalt, and their alloys; and reacting said feed in said reaction vessel at a temperature of from about 500° C. to 800° C. and a pressure of from about 101 kPa to 7000 kPa to produce a mixture of conversion products of said $CHClF_2$ which comprises at least 5 mole percent $C_2H_2F_4$, wherein the mole ratio of $CH_2FCF_3$ to $CHF_2CHF_2$ in said $C_2H_2F_4$ is at least about 1:9.

18. The process of claim 17 wherein the reaction vessel is an essentially empty reaction vessel; wherein the feed is reacted at a temperature of from about 550° C. to 725° C.; and wherein the mixture of conversion products includes at least 10 mole percent $C_2H_2F_4$ wherein the mole ratio of $CH_2FCF_3$ to $CHF_2CHF_2$ in the $C_2H_2F_4$ is at least about 1:9.

19. The process of claim 17 wherein $CF_2HCF_2CF_2H$, $CH_2F_2$ and $C_2H_2F_4$ are all produced.

20. The process of claim 19 wherein about 2 moles of $H_2$ are fed per mole C—Cl bond.

* * * * *